United States Patent
Kuslich

(10) Patent No.: US 8,012,211 B2
(45) Date of Patent: Sep. 6, 2011

(54) SEMI-BIOLOGICAL INTERVERTEBRAL DISC REPLACEMENT SYSTEM

(75) Inventor: Stephen D. Kuslich, Grant Township, MN (US)

(73) Assignee: Spineology, Inc., St. Paul, MN (US)

( * ) Notice: Subject to any disclaimer, the term of this patent is extended or adjusted under 35 U.S.C. 154(b) by 173 days.

(21) Appl. No.: 12/247,760

(22) Filed: Oct. 8, 2008

(65) Prior Publication Data

US 2009/0125110 A1    May 14, 2009

Related U.S. Application Data

(62) Division of application No. 10/702,096, filed on Nov. 5, 2003, now abandoned.

(60) Provisional application No. 60/423,900, filed on Nov. 5, 2002.

(51) Int. Cl.
*A61F 2/44* (2006.01)

(52) U.S. Cl. .................................................. 623/17.12

(58) Field of Classification Search .... 623/17.11–17.16, 623/23.72–23.76, 16.11, 14.12; 606/92–94, 606/60, 247–249, 99

See application file for complete search history.

(56) References Cited

U.S. PATENT DOCUMENTS

| | | | |
|---|---|---|---|
| 3,030,951 A | 4/1962 | Mandarino | |
| 3,867,728 A | 2/1975 | Stubstad et al. | |
| 3,875,595 A * | 4/1975 | Froning | 623/17.12 |
| 4,655,777 A | 4/1987 | Dunn et al. | |
| 4,735,625 A | 4/1988 | Davidson | |
| 4,755,184 A | 7/1988 | Silverberg | |
| 4,772,287 A * | 9/1988 | Ray et al. | 623/17.12 |
| 4,863,477 A | 9/1989 | Monson | |
| 4,904,260 A * | 2/1990 | Ray et al. | 623/17.12 |
| 4,932,969 A | 6/1990 | Frey et al. | |
| 4,932,975 A | 6/1990 | Main et al. | |
| 4,936,848 A | 6/1990 | Bagby | |
| 4,969,888 A | 11/1990 | Scholten et al. | |
| 5,015,255 A | 5/1991 | Kuslich | |
| 5,030,233 A | 7/1991 | Ducheyne | |
| 5,047,055 A | 9/1991 | Bao et al. | |
| 5,059,193 A | 10/1991 | Kuslich | |
| 5,108,404 A * | 4/1992 | Scholten et al. | 606/94 |
| 5,108,438 A | 4/1992 | Stone | |
| 5,133,767 A | 7/1992 | Frey et al. | |
| 5,147,359 A | 9/1992 | Cozad et al. | |
| 5,147,360 A | 9/1992 | Dubousset | |

(Continued)

FOREIGN PATENT DOCUMENTS

CA     2504591     5/2004

(Continued)

OTHER PUBLICATIONS

Kuslich et al., "The Origin of Low Back Pain and Sciatica: A Microsurgical Investigation" Chapter 1, *Microsurgery of the Lumbar Spine*, 1990, pp. 1-7.

(Continued)

*Primary Examiner* — Alvin J Stewart
(74) *Attorney, Agent, or Firm* — Skaar Ulbrich Macari, P.A.

(57) ABSTRACT

The present invention is a system for a partially biological disc replacement that stimulates natural fibrous, cartilaginous or other tissue growth in the DDD cavity, resulting in a partial biological disc replacement. Multiplicities of fibrous pieces of fibro-cartilaginous tissue promoting material are inserted into the DDD cavity inducing tissue growth.

7 Claims, 10 Drawing Sheets

U.S. PATENT DOCUMENTS

| | | | |
|---|---|---|---|
| 5,154,718 A | 10/1992 | Cozad et al. | |
| 5,171,280 A | 12/1992 | Baumgartner | |
| 5,171,281 A | 12/1992 | Parsons et al. | |
| 5,176,678 A | 1/1993 | Tsou | |
| 5,176,680 A | 1/1993 | Vignaud et al. | |
| 5,190,543 A | 3/1993 | Schläpfer | |
| 5,192,326 A | 3/1993 | Bao et al. | |
| 5,207,678 A | 5/1993 | Harms et al. | |
| 5,261,907 A | 11/1993 | Vignaud et al. | |
| 5,261,913 A | 11/1993 | Marnay | |
| 5,275,600 A | 1/1994 | Allard et al. | |
| 5,282,801 A | 2/1994 | Sherman | |
| 5,282,863 A | 2/1994 | Burton | |
| 5,306,307 A | 4/1994 | Senter et al. | |
| 5,306,308 A | 4/1994 | Gross et al. | |
| 5,306,309 A | 4/1994 | Wagner et al. | |
| 5,306,310 A | 4/1994 | Siebels | |
| 5,306,311 A | 4/1994 | Stone et al. | |
| 5,314,477 A | 5/1994 | Marnay | |
| 5,314,478 A | 5/1994 | Oka et al. | |
| 5,437,834 A | 8/1995 | Okimatsu et al. | |
| 5,503,164 A | 4/1996 | Friedman | |
| 5,549,679 A | 8/1996 | Kuslich | |
| 5,556,429 A | 9/1996 | Felt | |
| 5,562,736 A * | 10/1996 | Ray et al. | 606/86 A |
| 5,571,189 A * | 11/1996 | Kuslich | 623/17.12 |
| 5,634,945 A | 6/1997 | Pernia et al. | |
| 5,645,597 A * | 7/1997 | Krapiva | 606/279 |
| 5,827,289 A | 10/1998 | Reiley et al. | |
| 5,888,220 A | 3/1999 | Felt et al. | |
| 5,919,235 A | 7/1999 | Husson et al. | |
| 5,961,554 A | 10/1999 | Janson et al. | |
| 6,022,376 A * | 2/2000 | Assell et al. | 623/17.16 |
| 6,066,154 A * | 5/2000 | Reiley et al. | 606/192 |
| 6,110,210 A * | 8/2000 | Norton et al. | 623/17.16 |
| 6,113,639 A * | 9/2000 | Ray et al. | 623/17.16 |
| 6,127,597 A | 10/2000 | Beyar et al. | |
| 6,132,465 A * | 10/2000 | Ray et al. | 623/17.16 |
| 6,183,518 B1 * | 2/2001 | Ross et al. | 623/17.16 |
| 6,187,043 B1 * | 2/2001 | Ledergerber | 623/8 |
| 6,187,048 B1 | 2/2001 | Milner et al. | |
| 6,224,630 B1 | 5/2001 | Bao et al. | |
| 6,235,043 B1 * | 5/2001 | Reiley et al. | 606/192 |
| 6,240,926 B1 | 6/2001 | Chin Gan et al. | |
| 6,241,734 B1 | 6/2001 | Scribner et al. | |
| 6,245,107 B1 | 6/2001 | Ferree | |
| 6,248,110 B1 | 6/2001 | Reiley et al. | |
| 6,248,131 B1 * | 6/2001 | Felt et al. | 623/17.12 |
| 6,264,659 B1 * | 7/2001 | Ross et al. | 606/93 |
| 6,306,177 B1 | 10/2001 | Felt et al. | |
| 6,375,659 B1 * | 4/2002 | Erbe et al. | 606/94 |
| 6,383,190 B1 | 5/2002 | Preissman | |
| 6,395,034 B1 | 5/2002 | Suddaby | |
| 6,419,704 B1 * | 7/2002 | Ferree | 623/17.12 |
| 6,428,576 B1 * | 8/2002 | Haldimann | 623/17.16 |
| 6,436,143 B1 * | 8/2002 | Ross et al. | 623/17.16 |
| 6,437,018 B1 | 8/2002 | Gertzman et al. | |
| 6,443,988 B2 | 9/2002 | Felt et al. | |
| 6,482,235 B1 | 11/2002 | Lambrecht et al. | |
| 6,508,839 B1 * | 1/2003 | Lambrecht et al. | 623/17.16 |
| 6,533,817 B1 * | 3/2003 | Norton et al. | 623/17.16 |
| 6,592,625 B2 | 7/2003 | Cauthen | |
| 6,602,291 B1 * | 8/2003 | Ray et al. | 623/17.11 |
| 6,620,196 B1 * | 9/2003 | Trieu | 623/17.16 |
| 6,632,235 B2 * | 10/2003 | Weikel et al. | 606/192 |
| 6,663,647 B2 * | 12/2003 | Reiley et al. | 606/192 |
| 6,733,531 B1 * | 5/2004 | Trieu | 623/17.11 |
| 6,733,533 B1 * | 5/2004 | Lozier | 623/17.12 |
| 6,783,546 B2 * | 8/2004 | Zucherman et al. | 623/17.16 |
| 6,852,095 B1 | 2/2005 | Ray | |
| 6,869,445 B1 | 3/2005 | Johnson | |
| 6,878,155 B2 * | 4/2005 | Sharkey et al. | 607/96 |
| 6,893,466 B2 * | 5/2005 | Trieu | 623/17.16 |
| 6,899,719 B2 * | 5/2005 | Reiley et al. | 606/192 |
| 6,932,843 B2 * | 8/2005 | Smith et al. | 623/17.11 |
| 6,979,341 B2 * | 12/2005 | Scribner et al. | 606/192 |
| 6,981,981 B2 * | 1/2006 | Reiley et al. | 606/192 |
| 7,001,431 B2 * | 2/2006 | Bao et al. | 623/17.12 |
| 7,004,970 B2 * | 2/2006 | Cauthen, III et al. | 623/17.16 |
| 7,044,954 B2 | 5/2006 | Reiley et al. | 606/93 |
| 7,056,345 B2 * | 6/2006 | Kuslich | 623/17.16 |
| 7,066,960 B1 * | 6/2006 | Dickman | 623/17.16 |
| 7,077,865 B2 * | 7/2006 | Bao et al. | 623/17.12 |
| 7,156,877 B2 * | 1/2007 | Lotz et al. | 623/17.16 |
| 7,172,628 B2 * | 2/2007 | Lamprich et al. | 623/17.16 |
| 7,201,774 B2 * | 4/2007 | Ferree | 623/17.11 |
| 7,220,282 B2 * | 5/2007 | Kuslich | 623/17.16 |
| 7,226,481 B2 | 6/2007 | Kuslich | |
| 7,306,610 B2 * | 12/2007 | Chern Lin et al. | 606/92 |
| 7,318,840 B2 * | 1/2008 | McKay | 623/17.11 |
| 7,465,318 B2 * | 12/2008 | Sennett et al. | 623/17.12 |
| 7,503,936 B2 * | 3/2009 | Trieu | 623/17.16 |
| 7,507,243 B2 * | 3/2009 | Lambrecht et al. | 606/99 |
| 7,520,888 B2 * | 4/2009 | Trieu | 606/279 |
| 7,534,268 B2 * | 5/2009 | Hudgins et al. | 623/17.12 |
| 7,544,196 B2 * | 6/2009 | Bagga et al. | 606/93 |
| 7,575,577 B2 * | 8/2009 | Boyd et al. | 606/92 |
| 7,597,714 B2 * | 10/2009 | Suddaby | 623/17.16 |
| 7,601,157 B2 * | 10/2009 | Boyd et al. | 606/92 |
| 7,618,457 B2 * | 11/2009 | Hudgins | 623/17.12 |
| 7,618,461 B2 * | 11/2009 | Trieu | 623/17.16 |
| 7,628,800 B2 * | 12/2009 | Sherman et al. | 606/279 |
| 7,641,691 B2 * | 1/2010 | Lotz et al. | 623/17.12 |
| 7,645,301 B2 * | 1/2010 | Hudgins et al. | 623/17.12 |
| 7,666,205 B2 * | 2/2010 | Weikel et al. | 606/192 |
| 7,713,301 B2 * | 5/2010 | Bao et al. | 623/17.12 |
| 7,713,303 B2 * | 5/2010 | Trieu et al. | 623/17.16 |
| 7,758,644 B2 * | 7/2010 | Trieu | 623/17.11 |
| 7,758,647 B2 * | 7/2010 | Arnin et al. | 623/17.16 |
| 7,766,965 B2 * | 8/2010 | Bao et al. | 623/17.12 |
| 7,780,734 B2 * | 8/2010 | Johnson et al. | 623/17.16 |
| 7,785,368 B2 * | 8/2010 | Schaller | 623/17.11 |
| 7,789,912 B2 * | 9/2010 | Manzi et al. | 623/17.11 |
| 7,799,056 B2 * | 9/2010 | Sankaran | 606/246 |
| 7,799,078 B2 * | 9/2010 | Embry et al. | 623/17.11 |
| 7,799,079 B2 * | 9/2010 | Hestad et al. | 623/17.12 |
| 7,799,833 B2 * | 9/2010 | Boyd | 514/564 |
| 7,837,733 B2 * | 11/2010 | Collins et al. | 623/17.12 |
| 7,842,040 B2 * | 11/2010 | Rabiner et al. | 606/92 |
| 7,842,095 B2 * | 11/2010 | Klein | 623/23.19 |
| 7,883,511 B2 * | 2/2011 | Fernyhough | 606/92 |
| 7,887,593 B2 * | 2/2011 | McKay et al. | 623/17.16 |
| 7,901,460 B2 * | 3/2011 | Sherman | 623/17.16 |
| 7,914,537 B2 * | 3/2011 | Boyd et al. | 606/92 |
| 2002/0026195 A1 * | 2/2002 | Layne et al. | 606/72 |
| 2002/0026244 A1 | 2/2002 | Trieu | |
| 2002/0045942 A1 | 4/2002 | Ham | |
| 2002/0049449 A1 * | 4/2002 | Bhatnagar et al. | 606/94 |
| 2002/0068974 A1 | 6/2002 | Kuslich et al. | |
| 2002/0077701 A1 | 6/2002 | Kuslich | |
| 2002/0147496 A1 * | 10/2002 | Belef et al. | 623/17.12 |
| 2002/0147497 A1 * | 10/2002 | Belef et al. | 623/17.12 |
| 2002/0173851 A1 * | 11/2002 | McKay | 623/17.11 |
| 2002/0193813 A1 * | 12/2002 | Helkowski et al. | 606/151 |
| 2003/0181931 A1 * | 9/2003 | Dieck et al. | 606/157 |
| 2004/0054413 A1 * | 3/2004 | Higham et al. | 623/17.16 |
| 2004/0059417 A1 * | 3/2004 | Smith et al. | 623/17.11 |
| 2004/0068268 A1 * | 4/2004 | Boyd et al. | 606/92 |
| 2004/0106999 A1 * | 6/2004 | Mathews | 623/17.16 |
| 2004/0109823 A1 * | 6/2004 | Kaplan | 424/1.11 |
| 2004/0167625 A1 * | 8/2004 | Beyar et al. | 623/11.11 |
| 2004/0215343 A1 | 10/2004 | Hochschuler et al. | |
| 2005/0010297 A1 * | 1/2005 | Watson et al. | 623/17.12 |
| 2005/0015150 A1 * | 1/2005 | Lee | 623/17.12 |
| 2005/0049604 A1 * | 3/2005 | Singer et al. | 606/90 |
| 2005/0055094 A1 | 3/2005 | Kuslich | |
| 2005/0065609 A1 * | 3/2005 | Wardlaw | 623/17.12 |
| 2005/0090901 A1 * | 4/2005 | Studer | 623/17.12 |
| 2005/0182418 A1 * | 8/2005 | Boyd et al. | 606/92 |
| 2005/0209595 A1 * | 9/2005 | Karmon | 606/76 |
| 2005/0234498 A1 * | 10/2005 | Gronemeyer et al. | 606/192 |
| 2005/0245938 A1 * | 11/2005 | Kochan | 606/92 |
| 2005/0251259 A1 * | 11/2005 | Suddaby | 623/17.12 |
| 2006/0085069 A1 * | 4/2006 | Kim | 623/17.11 |
| 2006/0106461 A1 * | 5/2006 | Embry et al. | 623/17.12 |
| 2006/0122704 A1 * | 6/2006 | Vresilovic et al. | 623/17.16 |
| 2006/0149279 A1 * | 7/2006 | Mathews | 606/90 |

| | | | | |
|---|---|---|---|---|
| 2006/0149380 A1* | 7/2006 | Lotz et al. | | 623/17.12 |
| 2006/0173545 A1* | 8/2006 | Cauthen et al. | | 623/17.16 |
| 2006/0195115 A1* | 8/2006 | Ferree | | 606/92 |
| 2006/0253202 A1* | 11/2006 | Lipov | | 623/17.16 |
| 2006/0255503 A1* | 11/2006 | Higham et al. | | 264/255 |
| 2007/0055265 A1* | 3/2007 | Schaller | | 606/86 |
| 2007/0055272 A1* | 3/2007 | Schaller | | 606/90 |
| 2007/0093899 A1* | 4/2007 | Dutoit et al. | | 623/17.11 |
| 2007/0173943 A1* | 7/2007 | Dulak et al. | | 623/17.16 |
| 2007/0233222 A1* | 10/2007 | Roeder et al. | | 623/1.11 |
| 2008/0051800 A1* | 2/2008 | Diaz et al. | | 606/92 |
| 2008/0091199 A1* | 4/2008 | Cragg | | 606/60 |
| 2008/0103505 A1* | 5/2008 | Fransen | | 606/92 |
| 2008/0132899 A1* | 6/2008 | Shadduck et al. | | 606/94 |
| 2008/0140084 A1* | 6/2008 | Osorio et al. | | 606/94 |
| 2008/0249604 A1* | 10/2008 | Donovan et al. | | 623/1.15 |
| 2008/0269761 A1* | 10/2008 | Truckai et al. | | 606/94 |
| 2008/0269795 A1* | 10/2008 | Reiley et al. | | 606/192 |
| 2008/0269796 A1* | 10/2008 | Reiley et al. | | 606/192 |
| 2009/0069899 A1* | 3/2009 | Klein | | 623/22.4 |
| 2009/0076518 A1* | 3/2009 | Bowman et al. | | 606/93 |
| 2009/0125031 A1* | 5/2009 | Melsheimer et al. | | 606/94 |
| 2009/0125110 A1 | 5/2009 | Kuslich | | |
| 2010/0137990 A1* | 6/2010 | Apatsidis et al. | | 623/17.16 |
| 2010/0168859 A1* | 7/2010 | Wardlaw | | 623/17.12 |
| 2010/0174375 A1* | 7/2010 | Schaller | | 623/17.16 |
| 2010/0185286 A1* | 7/2010 | Allard et al. | | 623/17.11 |
| 2010/0222824 A1* | 9/2010 | Simonson | | 606/279 |
| 2010/0233234 A1* | 9/2010 | Arinzeh et al. | | 424/423 |
| 2010/0256646 A1* | 10/2010 | Pinal et al. | | 606/92 |
| 2010/0256647 A1* | 10/2010 | Trieu | | 606/92 |
| 2011/0009971 A1* | 1/2011 | Johnson et al. | | 623/17.16 |

FOREIGN PATENT DOCUMENTS

| | | |
|---|---|---|
| EP | 1 562 524 | 8/2005 |
| JP | 11-506658 | 6/1996 |
| JP | 10-501710 | 2/1998 |
| JP | 11-506657 | 6/1999 |
| WO | WO95/31948 | 11/1995 |
| WO | WO96/40015 | 12/1996 |
| WO | WO96/40020 | 12/1996 |
| WO | WO01/45577 A2 | 6/2001 |
| WO | WO02/054978 A2 | 7/2002 |
| WO | WO 2004/041075 A2 | 5/2004 |

OTHER PUBLICATIONS

Kuslich, "Microsurgical Lumbar Nerve Root Decompression Utilizing Progressive Local Anesthesia" Chapter 14, *Microsurgery of the Lumbar Spine*, 1990, pp. 139-147.

Kadoya et al., "Biomechanical and Morphologic Evaluation of a Three-Dimensional Fabric Sheep Artificial Intervertebral Disc", *Spine*, vol. 26, No. 14, Mar. 26, 2001, pp. 1562-1569.

File History for U.S. Patent No. 5,571,189, Issued Nov. 5, 1996.

File History for U.S. Patent No. 7,226,481 B2, Issued Jun. 5, 2007.

File History for U.S. Publication No. 2005/0055094, Published Mar. 10, 2005.

File History for U.S. Appl. No. 60/423,900, filed Nov. 5, 2002.

Examiner's first report on patent Application No. 2009202358 by Spineology, Inc., Australian Patent Office, Aug. 9, 2010, 2 pages.

Requisition by Canadian Patent Office in Application No. 2,504,591 to Spineology, May 17, 2010, 2 pages.

Response to Requisition by Canadian Patent Office in Application No. 2,504,591 by Spineology, Nov. 16, 2010, 4 pages.

Supplementary European Search Report for Application EP 03 78 3208.6, Nov. 19, 2010, 3 pages.

Notice of Preliminary Rejection by Korean Intellectual Property Office for Application No. 10-2005-7007897, Sep. 27, 2010, 6 pages including translation.

Notification of reasons for refusal by Japanese Patent Office in Application No. 2004-550358, Jul. 28, 2009, 9 pages including translation.

Response to Decision of Rejection by Japanese Patent Office in Application No. 2004-550358 by Spineology Inc., Oct. 19, 2009, 18 pages including translations.

Notification of reasons for refusal by Japanese Patent Office in Application No. 2004-550358, Mar. 17, 2010, 6 pages including translation.

Examination Report by the Intellectual Property Office of New Zealand, Jun. 12, 2007, 2 pages.

Response to Examination Report by the Intellectual Property Office of New Zealand by Spineology Inc., Dec. 3, 2008, 10 pages.

* cited by examiner

SEMI-BIOLOGICAL INTERVERTEBRAL DISC REPLACEMENT SYSTEM

RELATED APPLICATION

This application is a division of application Ser. No. 10/702,096 filed Nov. 5, 2003, which claims the benefit of U.S. Provisional Application No. 60/423,900 filed Nov. 5, 2002, each of which is hereby fully incorporated herein by reference.

FIELD OF THE INVENTION

The present invention relates generally to the field of systems adapted to replacing or assisting bone of a natural vertebral column of a living body. More specifically, the present invention relates to a system that surgeons can use to construct a semi-biological nuclear replacement that will replace the diseased nucleus and ultimately function in a manner similar to a natural disc nucleus.

BACKGROUND OF THE INVENTION

Low back pain is a condition affecting millions of humans. This syndrome causes great personal, economic and social hardship. Resultant consequences to family members, co-workers and the community are significant.

Scientific evidence indicates that the symptoms of low back pain are most commonly caused by degenerative pathology in the spinal motion segment. The spinal motion segment consists of a unit of spinal anatomy bounded by two vertebral bodies that includes the two vertebral bodies and the interposed intervertebral disc, as well as the attached ligaments, muscles and the facet joints. Degenerative pathology in the spinal motion segment is primarily related to intervertebral disc degeneration.

The fundamental causes of intervertebral disc degeneration are incompletely understood. However, scientific studies substantiate the following general conclusions about the sequential development of degenerative spinal pathology: The nucleus (the central cushion of the disc) loses nutritional support, dehydrates, and fragments. The loss in nutritional support causes nuclear tissue necrosis, the cells die. As the nuclear tissue dies, the pH in the nuclear region decreases and highly irritative chemicals form in the disc. Consequently, as the nucleus can no longer support compression loads, the annulus (the fibrous rim of the disc, surrounding the nucleus) is subjected to loading forces, in the form of compression and shear, that the annulus is poorly designed to handle.

Nociceptive nerve elements, i.e., pain generating, nerve ending afferents in the outer annulus, are stimulated by a combination of chemical and mechanical forces (leakage of irritative chemicals and compression and shear force on the annulus and spinal motion segment). These pain-detecting nerve elements propagate signals in the central and autonomic nervous system pathways, leading to the activation of central pain-modulating and pain-appreciating centers in the spinal cord and brain. The conscious portions of the brain interpret the resultant excitement of certain nerve centers in the spinal cord and brain as somatic and visceral pain.

The inventor and his team performed experimental studies directed to the tissue origin of spinal pain. The results of the inventor's observations, recorded during operations on humans undergoing spinal surgery under local anesthesia, conclusively demonstrated that the symptoms of mechanical low back pain originate when the outer portion of the degenerative intervertebral disc (and to a lesser extent, the capsule of the facet joint) is/are stimulated by mechanical forces. Kuslich, Stephen D., Ulstrom, Cynthia L.; "The Origin of Low Back Pain and Sciatica: A Microsurgical Investigation"; *Orthop Clin North Am* 1991 April; 22(2): 181-7.

For reasons that are not perfectly clear many, if not most, humans develop the aforementioned pathologic changes in the disc nucleus as they approach middle age. Breakdown products of the disc and facet joints stimulate sensitive nerve endings in and around the disc and facet capsule, producing low back pain, and sometimes, sciatica. This pathologic phenomenon is commonly referred to as Degenerative Disc Disease ("DDD"). Degenerative Disc Disease is the primary cause of low back pain. The DDD tissue consists of the dead and/or dying fibrocartilogenous remains of the disc nucleus and inner portions of the annulus. Various toxic chemicals— such as Substance P—have been detected in DDD discs. Other investigators have described low pH (acidity) of fluids in DDD tissue. These chemicals and fluids leak out through fissures and tears in the annulus and irritate and stimulate the nociceptive nerve endings causing back pain.

Although, effective means to prevent DDD do not exist, some relatively effective treatments for DDD do exist. A number of medical and surgical strategies are known to ameliorate symptoms. These include: pain medications that block or modulate pain afferents, or suppress central pain-recognition centers, exercises that promote tissue nutrition, flexibility and muscle strength (exercises also stimulate the release of endorphin, an endogenous morphine-like chemical), braces that restrict motion and reduce forces on tender spinal tissues, anti-inflammatory oral and injectable medications, and surgical procedures designed to remove tissues pressing on nerves, stabilize spinal motion segments and/or replace pathological tissues.

Most surgical procedures designed to relieve low back pain and sciatica involves removal of a portion of the intervertebral disc. Unfortunately, removing disc tissue leaves a void in the intervertebral space. The patient's pain following partial or complete disc removal may be more severe than the pain preceding the operation. Therefore, surgeons often perform additional operations that are intended to restabilize the spinal motion segment.

Strategies for restabilization are many and include: heating the annular region in an effort to destroy nerve endings and "strengthen" or "heal" the annulus, "fusing" the motion segment by applying bone graft on the sides of the motion segment, or within the disc space, applying rigid or semi-rigid support members on the sides of the motion segment or within the disc space, removing and replacing the entire disc with a non-flexible, articulating artificial device and removing and replacing the nucleus.

A number of artificial disc replacements have been developed. The currently available devices fall into two general categories: total disc replacements and nuclear replacements. The first category consists of total disc replacements that are made of rigid, inert substances such as metal and plastic. Examples of such devices are the Fernstrom "ball-bearing" and the LINK® and PRODISC® devices.

These types of artificial discs have five main disadvantages. First, is that the devices are relatively large and non-compressible, so they require relatively large surgical exposures, thereby increasing the chance of morbidity, including infection and hemorrhage. Second, because the devices are constructed from rigid inert metal and plastic materials, they can cause serious damage if they were to displace into positions normally occupied by local nervous or vascular tissues. Third, the device implantation requires the removal of a large portion of the annulus. Such removal greatly reduces the inherent stability of the motion segment, at least early on, before healing occurs around the implant. Fourth, these inert, rigid-component disc replacements do not reproduce natural disc mechanics. Finally, unless these devices become and remain firmly attached to the vertebral endplates, relative motion between the implant and the vertebral bone will cause erosion of the vertebral endplates, possibly leading to subsidence, instability and/or neurological or vascular damage.

A second class of disc replacement is the nuclear replacement, a form of partial disc replacement. Examples include: the Ray implant (U.S. Pat. No. 4,772,287), the Bao implant (U.S. Pat. No. 5,192,326), and the Sulzer spiral implant (U.S. Pat. No. 5,919,235).

These devices are also inert, somewhat flexible, non-biological disc replacements. They involve removal of the nucleus and replacement of the nucleus with a non-biological plastic material that may be flexible and malleable. When these devices are placed in the excavated DDD cavity, they rub against living end-plate cartilage and bone. This rubbing may cause healthy living tissue to erode. This erosion may weaken the living cartilage and bone, resulting in subsidence of the device, fragmentation of the device and perhaps, further vertebral instability. Complete displacement and dislocation of the Ray implant has been reported.

This second category of disc replacements is intended to more closely mimic natural disc mechanics. To accomplish this, some nuclear replacements utilize the water-containing properties of hydrogel. One embodiment of the Ray implant as described in U.S. Pat. Nos. 4,772,287 and 4,904,260 consists of a block of hydrogel in combination with inert jacket such as a plastic fabric casing. The Bao implant as described in U.S. Pat. No. 5,192,326 consists of hydrogel beads enclosed by a fabric shell.

Devices using large blocks of hydrogel and other inert substances have three main problems. First, there is a 10 to 50 percent extrusion rate of the prosthetic disc beyond the DDD cavity during the post-operative period. Second, because physiologic loads and movements continue after operation, this prosthetic device can erode into the intervertebral bone, increasing instability. Third, inserting the device requires a moderate sized surgical exposure.

Kotani, et al. at Hokkaido University in Japan are developing an artificial disc made of a preformed fabric matrix (*Spine* 2001; 26:1562-1569). The fabric matrix is intended to mimic the mechanics of a natural disc. However, this technology also has shortcomings. First, the device's insertion requires a large exposure with a loss of vertebral stabilizers, i.e., the relatively large area of annulus removed during implantation. Second, the device requires that a complex weaving procedure be undertaken during manufacture. Third, many different sizes will be required for different patients and procedures. Fourth, the device must be pre-sized to fit the cavity in the disc. Fifth, since its components contain no water-imbibing component, it cannot re-hydrate itself when local ambient pressures decrease. Thus, it cannot remain hydrated in response to diurnal rhythms and function as a natural disc would function.

Devices attempting to mimic the mechanics of a natural disc also include such devices as taught in U.S. Pat. No. 6,240,926 to Chin Gan et al. This patent uses a hybrid of cultured intervertebral disc cells and a biodegradable substrate as a nuclear replacement. The device attempts to induce intervertebral disc reformation by regenerating natural disc tissue via the introduction of cultured intervertebral disc cells. Technology such as this is in an early stage of development. Compared to the wide experience with biocompatible materials such as plastics and metals, purely biological replacements may or may not prove to be practical.

While numerous techniques and devices have been developed to stabilize a spinal motion segment in an effort to ameliorate the consequences of DDD, there is a continuing need for improvements in this field.

SUMMARY OF THE INVENTION

The present invention is a system for a partially biological disc replacement that stimulates natural fibrous, cartilaginous or other tissue growth in the DDD cavity, resulting in a partial biological disc replacement. Multiplicities of fibronous pieces of fibro-cartilaginous tissue promoting material are inserted into the DDD cavity inducing tissue growth. The fibro-cartilaginous tissue promoting material may be combined with hydrogel or other suitable water-imbibing material.

The present invention improves upon current techniques by creating a biological disc replacement that induces living, natural fibrous tissue growth into the DDD cavity. It is believed that living, natural fibrous tissue is preferable to dead and/or dying DDD tissue. First, living natural fibrous tissue does not exhibit acidic properties nor leak chemicals that may cause nerve inflammation and back pain. Second, living natural fibrous tissue offers more support and stability than decaying tissue.

Living natural fibrous tissue is also preferable to inert disc replacements. Living natural fibrous tissue will not erode adjacent cartilage or bone. Furthermore, there is less danger to surrounding tissues or nerves should the replaced material extrude from its intended position. Finally, living natural fibrous or fibro-cartilaginous tissue is more likely to mimic the biomechanical and morphologic characteristics of a natural disc.

The present invention replaces the dead and/or dying fibro-cartilage of a DDD disc by stimulating living natural fibrous tissue growth with a multiplicity of fibronous pieces, this living natural fibrous tissue fuses with the living tissue of the DDD cavity, forming a partial biological disc replacing the removed DDD tissue.

DETAILED DESCRIPTION OF THE PREFERRED EMBODIMENTS

Figure 1:
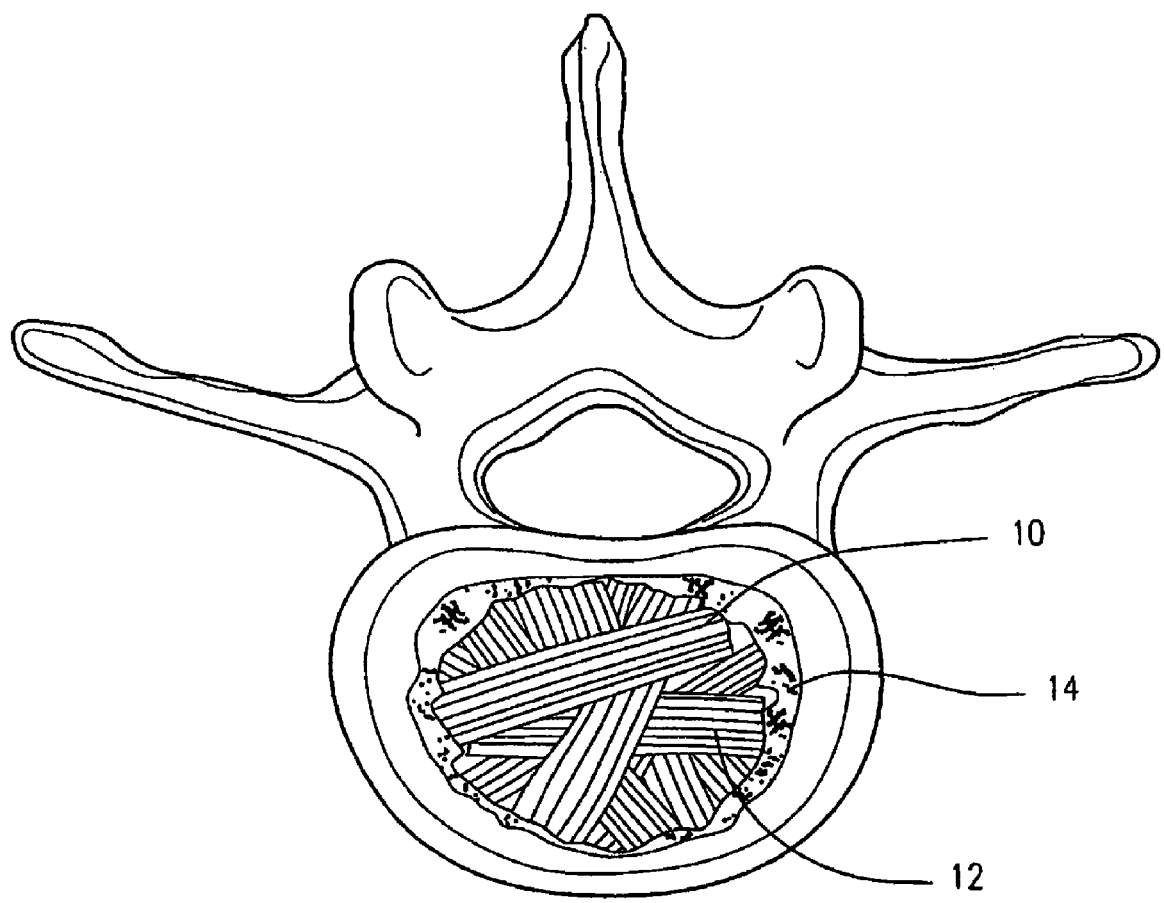
FIG. 1 is a perspective view of bands of fibro-cartilaginous tissue promoting material placed in a disc cavity.

The present invention mimics the biomechanics of a natural disc nucleus by inducing natural fibrous tissue growth. FIG. 1 depicts the device 10 of the present invention embodied in a preparation of multilayered bands of suitable fibrous tissue promoting material piled in a circular configuration 12 formed to fit securely in the DDD cavity 14. The suitable fibrous tissue promoting material may include, but is not limited to, autograft, allograft or xenograft of fascia lata and/or throraco-lumbar fascia; natural and/or manmade polymeric fiber; fibrous tissue inducers such as: talc, pharmaceuticals and/or minerals; fibrous tissue morphogenic protein produced by recombinant DNA technology and/or notochord cells from stem cell technology and/or any combination thereof.

Figure 2:
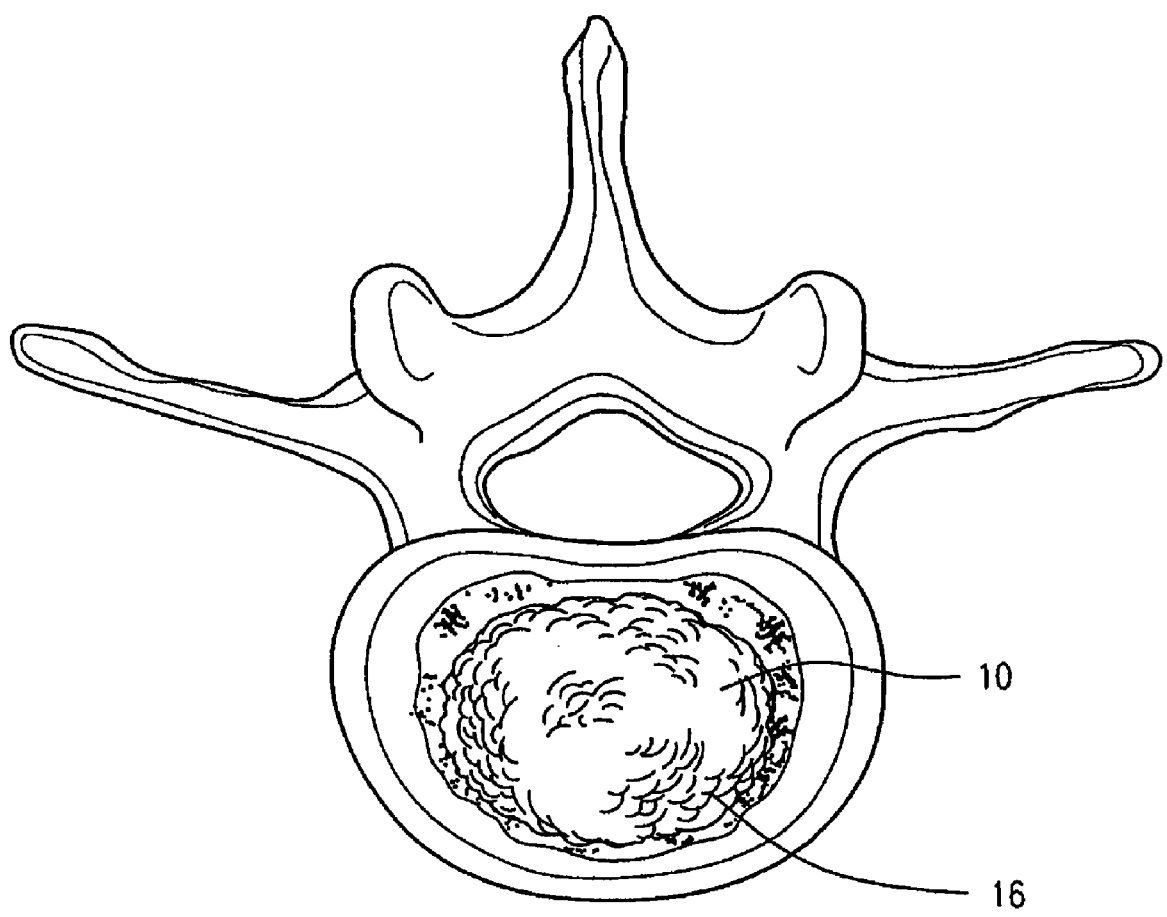
FIG. 2 is a perspective view of fibro-cartilaginous tissue promoting material placed in a disc cavity.
Figure 3:
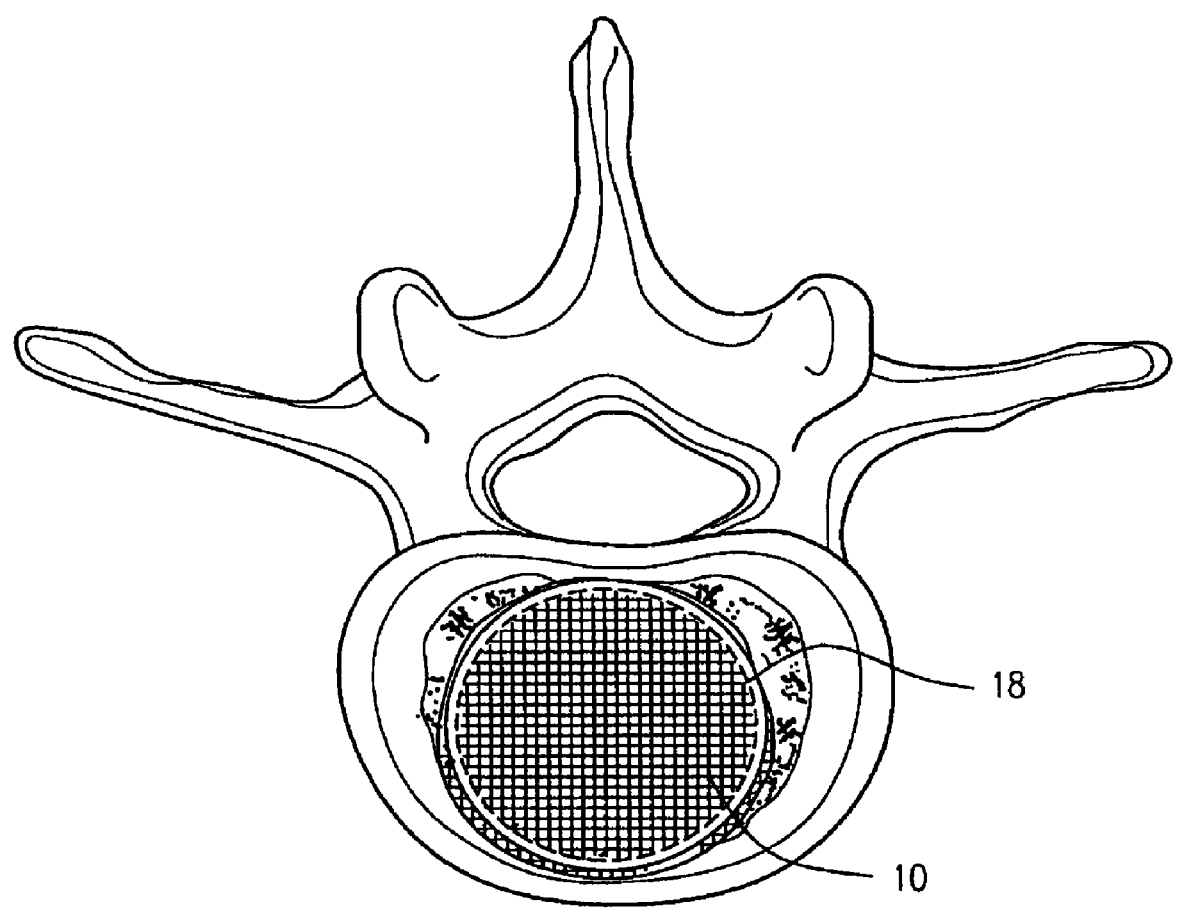
FIG. 3 is a perspective view of an OPTIMESH™ filled with fibro-cartilaginous tissue promoting material in a disc cavity.

FIG. 2 depicts another embodiment of the device 10 as a tangled knot of suitable fibrous tissue promoting fibers 16. In yet another embodiment, the device is multiple fabric bands made of suitable fibrous tissue promoting material. In another embodiment, the device is any combination of fibers, string, multilayered bands and/or fabric bands made of suitable fibrous tissue promoting material.

Figure 4:
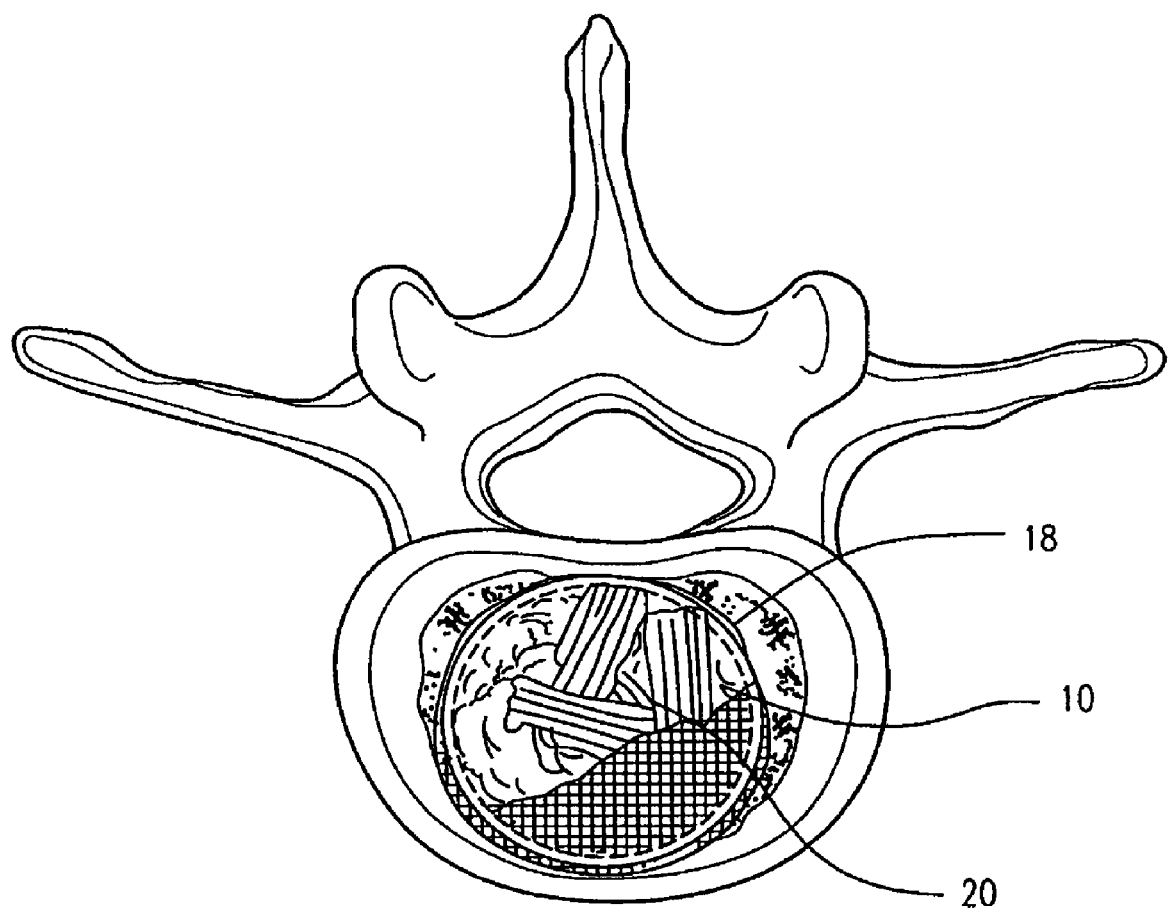
FIG. 4 is a cross-sectional view of an OPTIMESH™ filled with fibro-cartilaginous tissue promoting material in a disc cavity.
Figure 5:
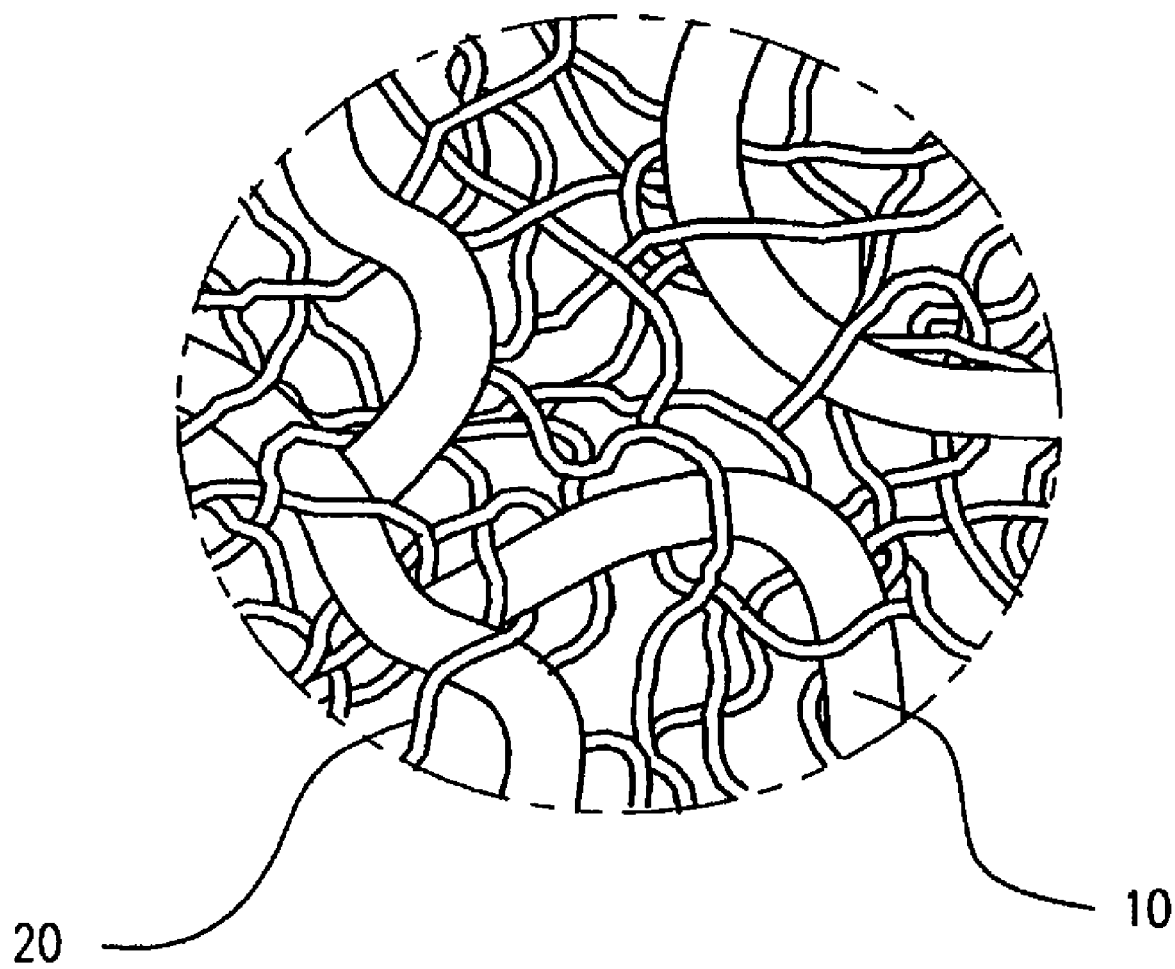
FIG. 5 is a perspective view of a mixture of cotton and hydrogel fibers.
Figure 6:
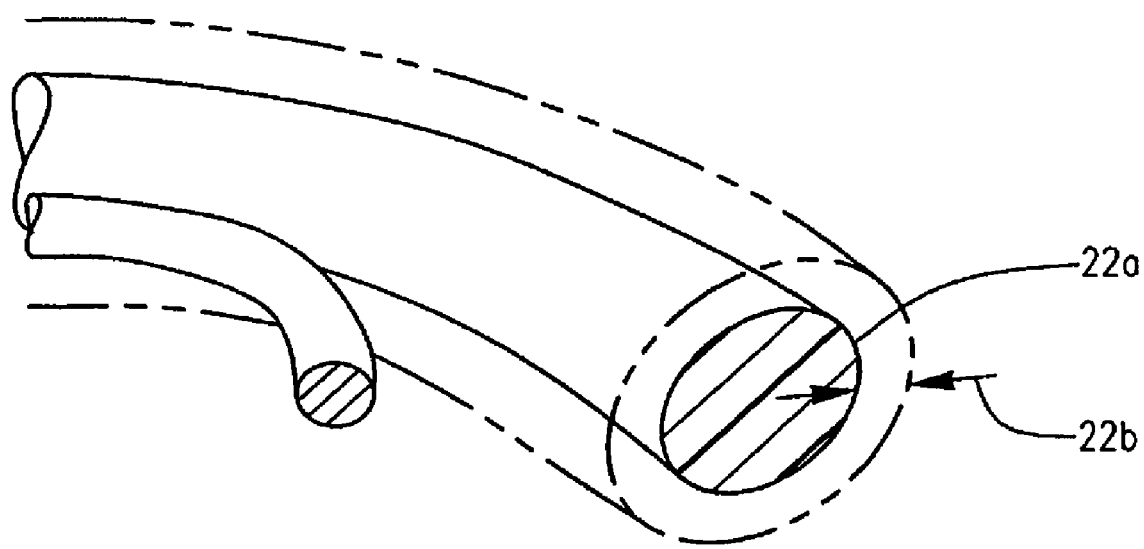
FIG. 6 is a cross-sectional depiction of the expansion of the hydrogel as the hydrogel absorbs fluid.
Figure 7:
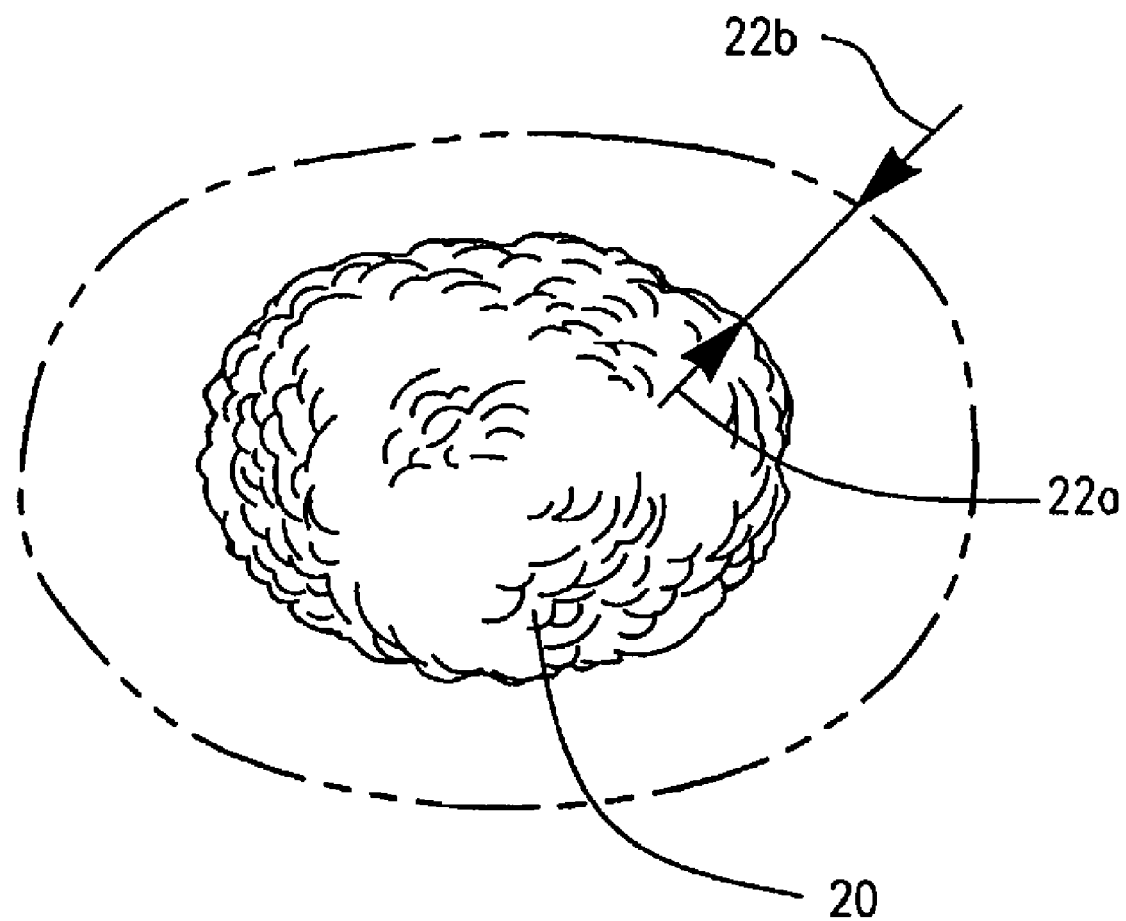
FIG. 7 is a perspective of the expansion of the mixture of fibro-cartilaginous tissue promoting material and hydrogel as the hydrogel absorbs fluid.

Finally, as depicted in FIGS. 4 and 5, another embodiment of the device is a preparation of suitable fibrous tissue promoting material in combination with hydrogel chunks and/or fibers 20. This embodiment has many advantages. The hydrogel provides water-imbibing qualities similar to a natural disc. The hydrogel thus provides a source of hydration for the device. As the hydrogel absorbs water, the hydrogel and thus the device expands. FIGS. 6 and 7 show the fluid expansion as arrows 22a and 22b. The suitable fibrous tissue promoting material induces living, natural fibrous tissue growth. The living, natural fibrous tissue gives stability and cushion to the DDD cavity. The combination of stability, cushioning and hydration allows the device of the present invention to closely mimic the characteristics of a natural disc.

Figure 8:
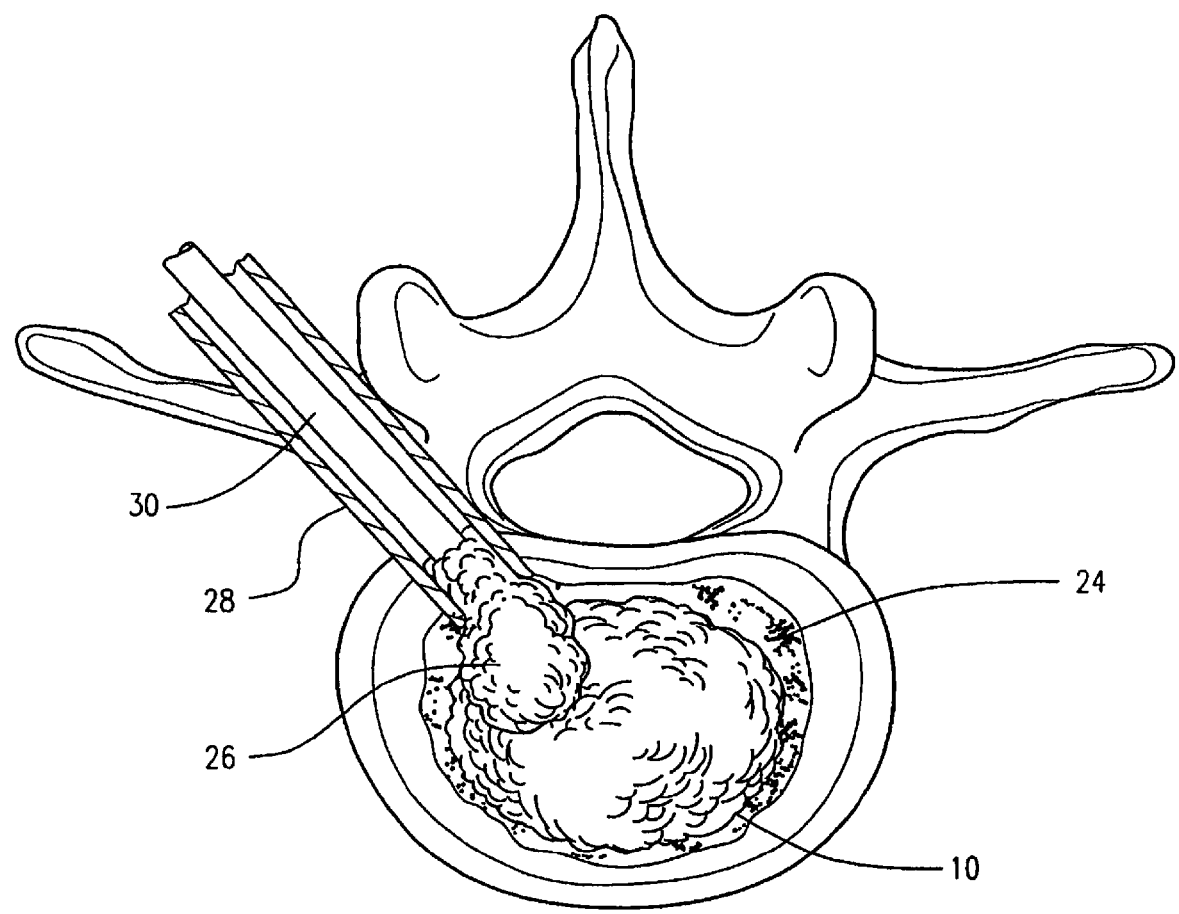
FIG. 8 depicts aliquots of the fibro-cartilaginous tissue promoting material and hydrogel being inserted by a piston through a small diameter tube into the disc cavity.

FIG. 8 depicts an important feature differentiating the present invention from all of its predecessors; the device is preferably constructed within the nuclear space 24, in a piecemeal fashion, by pushing small aliquots 26 of the filaments that make up the ultimate device, through a small diameter hollow injection tube 28. This feature allows the nuclear replacement device 10 to be introduced through a very small portal, with very little damage or removal of the stabilizing annulus.

Figure 9:
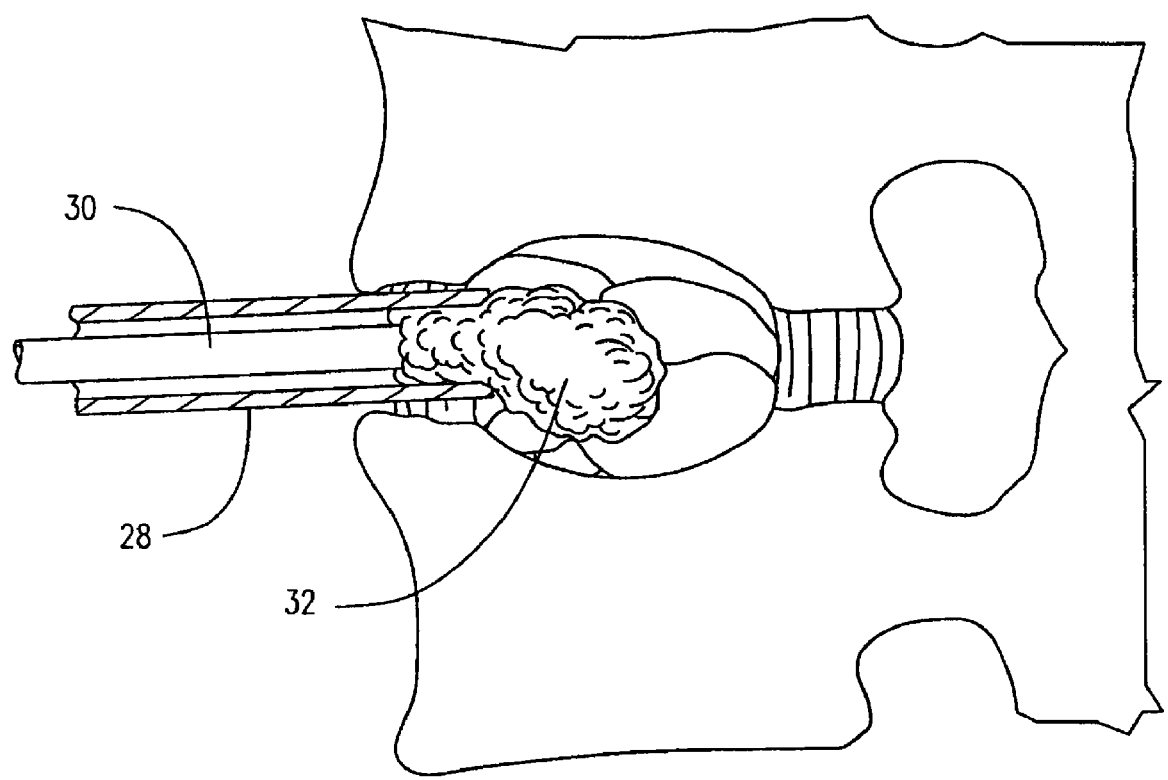
FIG. 9 is a cross-sectional view of the fibro-cartilaginous tissue promoting material and hydrogel being inserted by a piston through a small diameter tube into the disc cavity.
Figure 10:
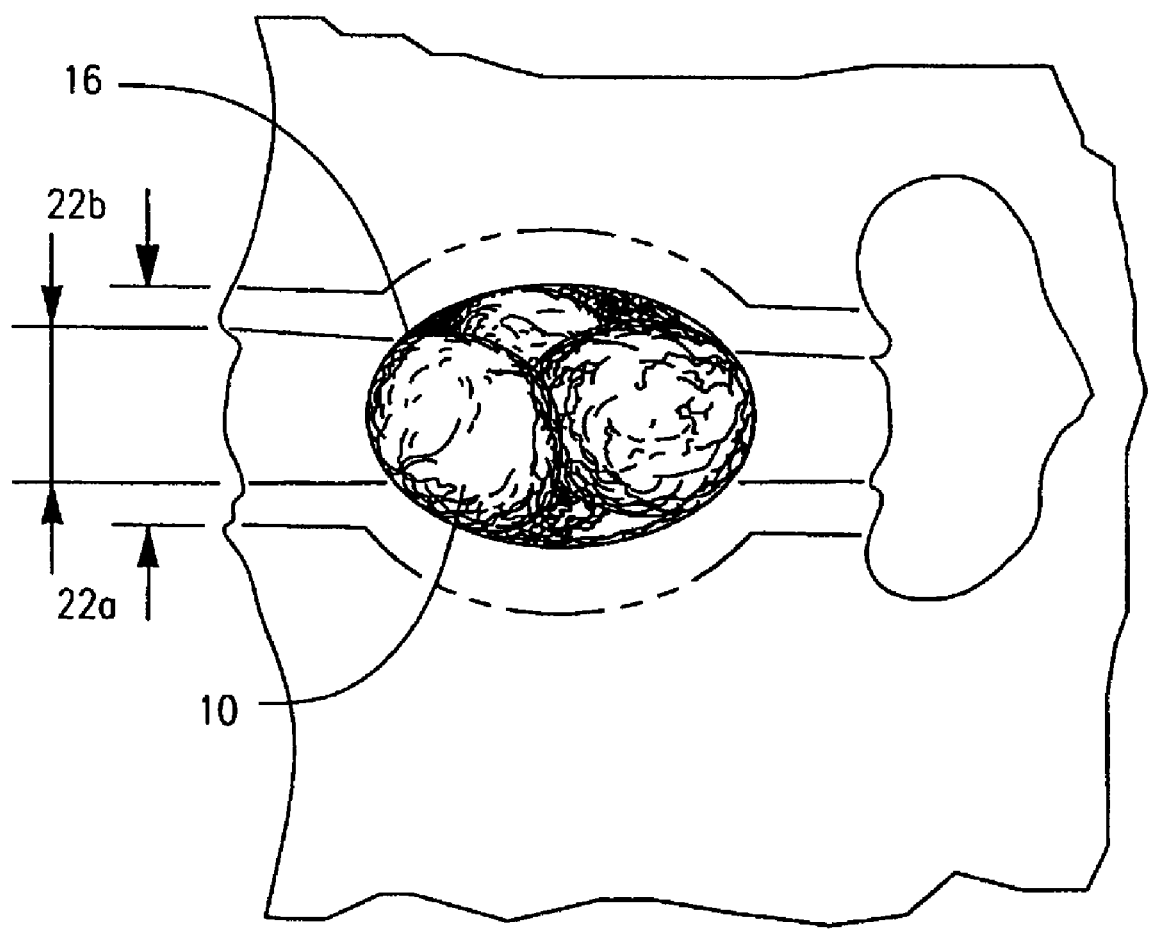
FIG. 10 is a cross-sectional view of the bundles of fibrocartilaginous tissue promoting material and hydrogel expanding as the hydrogel absorbs water.

FIG. 9 depicts an embodiment of the invention where the tissue promoting material 32 is at least one strand with a cross-sectional diameter smaller than the diameter of the injection tube 28. The invention is really a system, therefore, that allows the surgeon to construct a nuclear replacement using minimally invasive techniques. The system consists of a hollow injection tube 28, a piston 30, the filaments 26 (cotton or other fibrous tissue stimulating agents with or without hydrogel) and, in at least one embodiment, a fabric or other porous shell 18 that surrounds and contains the filamentous elements.

The method of the present invention involves boring a small entrance hole into the DDD cavity 14. This step can be accomplished using any of several approaches: posterior laminotomy, transforaminal, or any of the anterior or anterior-lateral approaches, including endoscopic approaches. The surgeon then reams the cavity 14 to remove the DDD nucleus and perhaps some of the endplate cartilage and portions of the inner annulus. The cavity 14 is thereby prepared for the optiplasty device insertion.

The cavity 14 may be prepared by coating its surface with talc, a pharmaceutical or other suitable fibrous tissue promoting material. The multiplicity of fibronous pieces of fibrocartilaginous tissue promoting material are then inserted using a piston 30 through a small diameter tube 28 and may or may not be secured within an Optimesh™, of U.S. Pat. No. 5,571,189 to the applicant, or any other suitable porous bag.

What is claimed:

1. A system for semi-biologic nuclear replacement for a degenerated disc of a spine of a mammalian body comprising:
    an injection tube having a small diameter corresponding to a small entrance hole defined in the degenerated disc that is at least partially excavated to create a cavity;
    a volume of strands of tissue promoting material combined with hydrogel strands sufficient to fill at least a portion of the cavity; and
    an insertion device operably coupled to the injection tube that dispenses the volume of strands of tissue promoting material combined with strands of hydrogel into the cavity in a piecemeal manner as a plurality of aliquots of the tissue promoting material and hydrogel strands.

2. The nuclear replacement of claim 1 wherein the tissue promoting material is selected from a group consisting of fibrous tissue promoting material, cartilaginous promoting material and any combination thereof.

3. The nuclear replacement of claim 1 wherein the tissue promoting material is a preparation of multilayered bands piled in a circular configuration.

4. The nuclear replacement of claim 1 wherein the tissue promoting material is a preparation of tangled knots.

5. The nuclear replacement of claim 1 wherein the tissue promoting material is a preparation of multiple fabric bands.

6. The nuclear replacement of claim 1 wherein the tissue promoting material is surrounded by a porous container.

7. The nuclear replacement of claim 1 wherein the tissue promoting material is selected from a group comprising: autograft, allograft, or xenograft of fascia, autograft, manmade polymeric fiber, talc, tissue promoting pharmaceuticals, tissue promoting minerals, tissue morphogenic protein, notochord cells and any combination thereof.

* * * * *